(12) United States Patent
Amerson

(10) Patent No.: US 9,713,548 B2
(45) Date of Patent: Jul. 25, 2017

(54) URINE COLLECTION ASSEMBLY

(71) Applicant: Sandra A. Amerson, Miramar, FL (US)

(72) Inventor: Sandra A. Amerson, Miramar, FL (US)

( * ) Notice: Subject to any disclaimer, the term of this patent is extended or adjusted under 35 U.S.C. 154(b) by 249 days.

(21) Appl. No.: 14/295,432

(22) Filed: Jun. 4, 2014

(65) Prior Publication Data
US 2015/0351953 A1    Dec. 10, 2015

(51) Int. Cl.
*A61F 5/44* (2006.01)
(52) U.S. Cl.
CPC .................. *A61F 5/4404* (2013.01)
(58) Field of Classification Search
CPC ........ A61F 5/453; A61F 5/451; A61F 13/471; A61F 13/70; A61F 2013/15146; A61F 5/4404; A61F 5/44; A61F 5/4401; A61F 5/541; A61F 5/455; A61F 2013/4593; A61F 2013/47281; A61B 10/007; A61B 10/0038
USPC .......................................................... 604/580
See application file for complete search history.

(56) References Cited

U.S. PATENT DOCUMENTS

| | | | | | |
|---|---|---|---|---|---|
| 1,426,429 | A | * | 8/1922 | Hale | B65B 11/004 |
| | | | | | 53/207 |
| 1,490,793 | A | * | 4/1924 | Ajamian | A61F 5/453 |
| | | | | | 119/869 |
| 2,837,095 | A | * | 6/1958 | Stevenson | A41B 13/04 |
| | | | | | 604/354 |
| 3,532,093 | A | * | 10/1970 | Lovret | A61F 5/451 |
| | | | | | 604/348 |
| 3,721,243 | A | * | 3/1973 | Hesterman | A61F 5/453 |
| | | | | | 604/185 |
| 4,305,405 | A | * | 12/1981 | Meisch | A61B 5/20 |
| | | | | | 53/157 |
| 6,375,643 | B1 | * | 4/2002 | Moorhead | A61B 10/007 |
| | | | | | 604/322 |
| 6,565,545 | B1 | * | 5/2003 | Frenche | A61F 5/453 |
| | | | | | 604/349 |
| 7,192,424 | B2 | | 3/2007 | Cooper | |
| 7,763,003 | B1 | | 7/2010 | Yip | |
| 8,324,445 | B2 | | 12/2012 | MacDonald et al. | |
| 2004/0220538 | A1 | | 11/2004 | Panopoulos | |
| 2004/0254547 | A1 | * | 12/2004 | Okabe | A61F 5/455 |
| | | | | | 604/317 |
| 2007/0142793 | A1 | * | 6/2007 | Ben Youssef | A61F 5/455 |
| | | | | | 604/329 |
| 2007/0185466 | A1 | | 8/2007 | Co | |
| 2008/0274014 | A1 | | 11/2008 | Jumonville et al. | |
| 2011/0178492 | A1 | | 7/2011 | Coates | |
| 2012/0283686 | A1 | | 11/2012 | Ramage | |
| 2013/0006206 | A1 | * | 1/2013 | Wada | A61F 13/535 |
| | | | | | 604/385.01 |

FOREIGN PATENT DOCUMENTS

WO    WO 2005003725 A2 *    1/2005    ........... A61B 10/007

* cited by examiner

*Primary Examiner* — Kathryn E Ditmer

(57) ABSTRACT

A urine collection assembly for collecting a urine sample from an infant wherein the urine is prevented from being spilled. The assembly includes a garment that may be worn about an infant's genital area. A reservoir is coupled to the garment. The reservoir may collect the urine from the infant. The reservoir is penetrable by a syringe. The urine is drawn into the syringe without spilling the urine from the reservoir.

7 Claims, 3 Drawing Sheets

URINE COLLECTION ASSEMBLY

BACKGROUND OF THE DISCLOSURE

Field of the Disclosure

The disclosure relates to collection devices and more particularly pertains to a new collection device for collecting a urine sample from an infant wherein the urine is prevented from being spilled.

SUMMARY OF THE DISCLOSURE

An embodiment of the disclosure meets the needs presented above by generally comprising a garment that may be worn about an infant's genital area. A reservoir is coupled to the garment. The reservoir may collect the urine from the infant. The reservoir is penetrable by a syringe. The urine is drawn into the syringe without spilling the urine from the reservoir.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
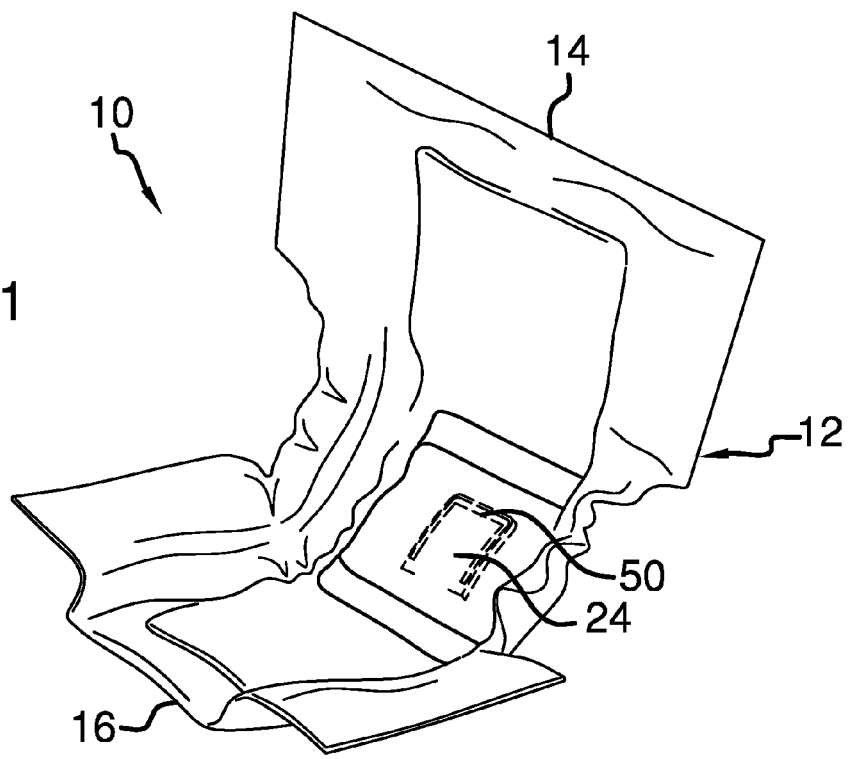
FIG. 1 is a perspective view of a urine collection assembly according to an embodiment of the disclosure.
Figure 2:
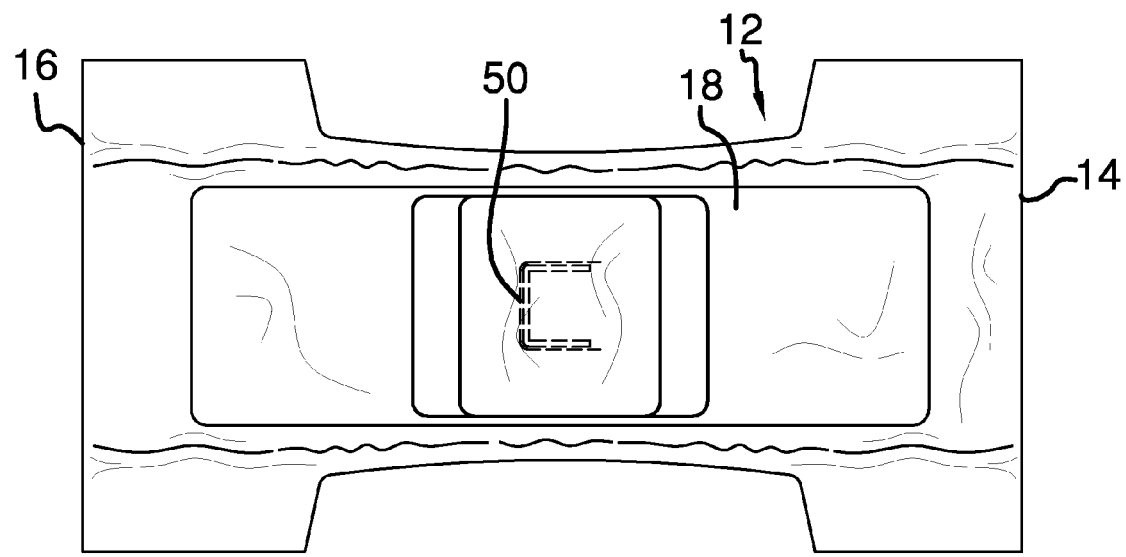
FIG. 2 is a top view of an embodiment of the disclosure.
Figure 3:
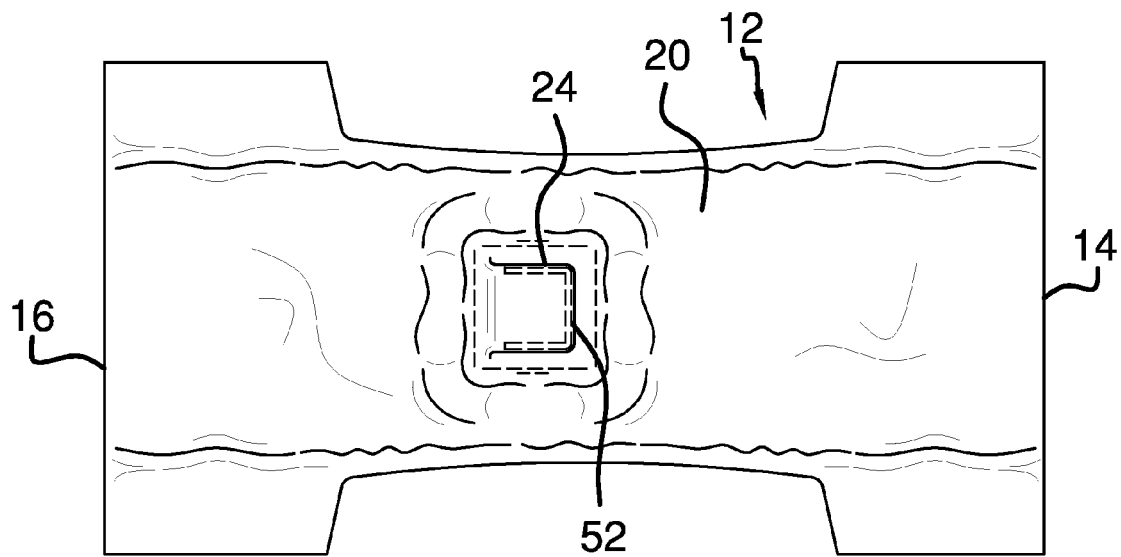
FIG. 3 is a bottom view of an embodiment of the disclosure.
Figure 4:
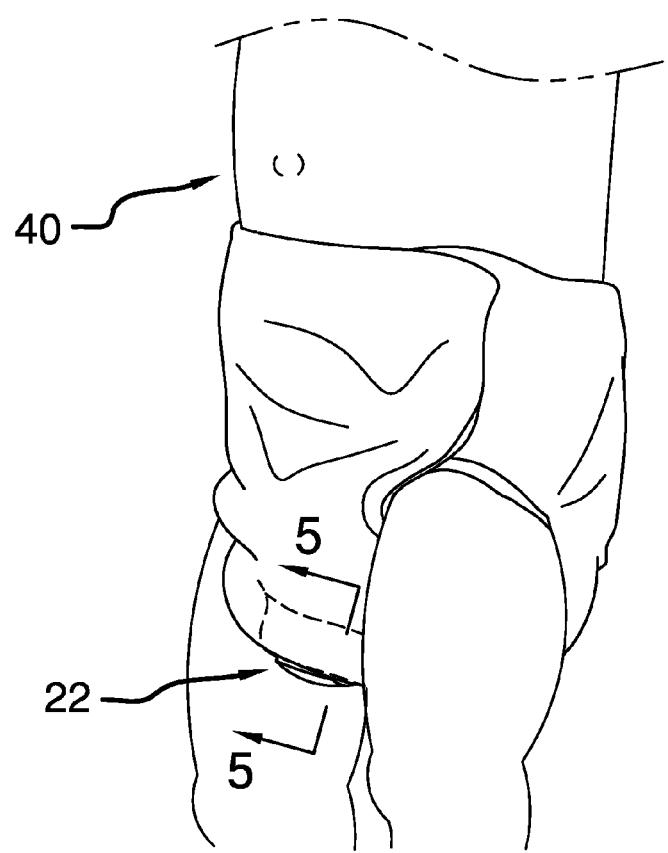
FIG. 4 is an in-use view of an embodiment of the disclosure.
Figure 5:
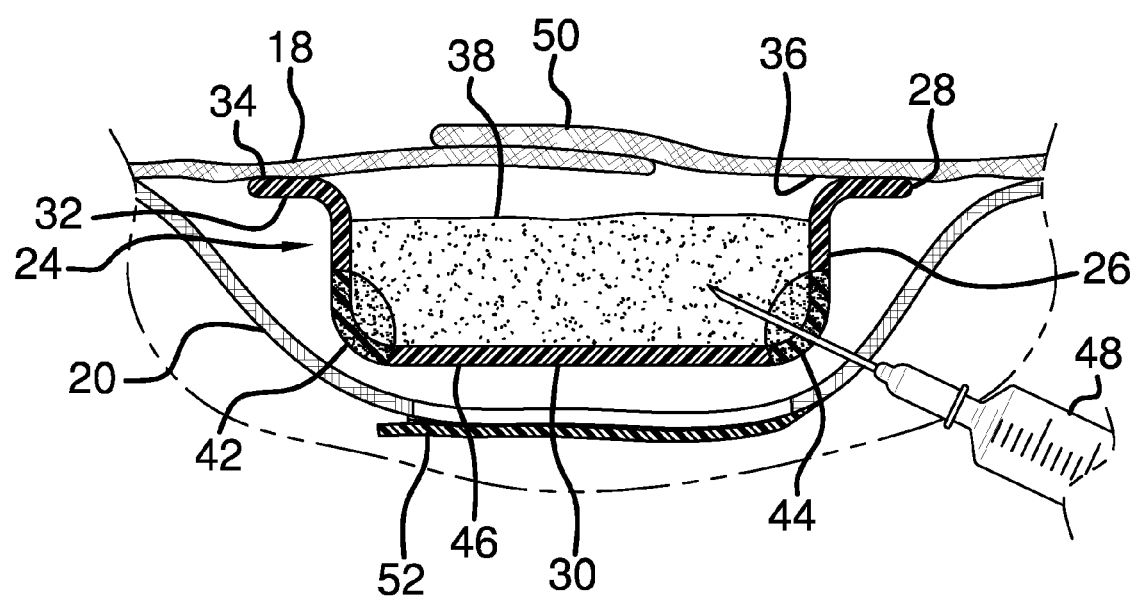
FIG. 5 is a cross sectional view taken along line 5-5 of FIG. 4 of an embodiment of the disclosure.

With reference now to the drawings, and in particular to FIGS. 1 through 5 thereof, a new collection device embodying the principles and concepts of an embodiment of the disclosure and generally designated by the reference numeral 10 will be described.

As best illustrated in FIGS. 1 through 5, the urine collection assembly 10 generally comprises a garment 12. The garment 12 has a first end 14 and a second end 16. The garment 12 is elongated. Additionally, the garment 12 has an uppermost wall 18 and a bottommost wall 20 each extending between the first 14 and second 16 ends of the garment 12. The uppermost 18 and lowermost 20 walls of the garment 12 are joined together at the first 14 and second 16 ends of the garment 12. The garment 12 may be worn about an infant's genital area 22. The garment 12 may be a diaper of any conventional design.

A reservoir 24 is provided. The reservoir 24 has an exterior wall 26 extending between a top end 28 and a bottom end 30 of the reservoir 24. The top end 28 of the reservoir 24 is open. The exterior wall 26 of the reservoir 24 flares outwardly at the top end 28 of the reservoir 24 to define a lip 32. An inside surface 34 of the lip 32 is coupled to a bottom surface 36 of the uppermost wall 18 of the garment 12. The reservoir 24 may collect urine 38 from the infant 40. Finally, the reservoir 24 is centrally positioned on the garment 12 so the reservoir 24 is positioned proximate the infant's genital area 22 when the garment 12 is worn.

Each of a first lateral edge 42 and a second lateral edge 44 of a bottom side 46 of the exterior wall 26 of the reservoir 24 is penetrable by a syringe 48. The urine 38 is drawn into the syringe 48 without spilling the urine 38 from the reservoir 24. Each of the first 42 and second 44 lateral edges of the bottom side 46 of the exterior wall 26 of the reservoir 24 may be comprised of a resiliently penetrable material. The urine 38 in the reservoir 24 is prevented from leaking after the syringe 48 is removed from the exterior wall 26 of the reservoir 24.

The uppermost wall 18 of the garment 12 has a first flap 50 positioned over the top end 28 of the reservoir 24. The first flap 50 is positionable in a closed position so the urine 38 is retained in the reservoir 24. Additionally, the first flap 50 is positionable in an open position to access an interior of the reservoir 24. The lowermost wall 20 of the garment 12 has a second flap 52 positioned over the bottom side 46 of the exterior wall 26 of the reservoir 24. The second flap 52 is positionable between an open position and a closed position.

In use, the garment 12 is worn by the infant 40 when a urine 38 sample needs to be collected from the infant 40. The garment 12 is removed from the infant 40 after the infant 40 urinates. The syringe 48 is inserted through a selected one of the first 42 or second 44 lateral edges of the bottom side 46 of the exterior wall 26 of the reservoir 24 to draw the urine 38 sample. After the urine 38 sample is drawn, the garment 12 may be disposed of.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A urine collection assembly comprising:
   a garment configured to be worn about the infant's genital area, said garment having an uppermost wall and a bottommost wall each extending between a first and a second end of said garment, an uppermost wall of said garment having a first flap positioned over a top end of a reservoir, a lowermost wall of said garment having a second flap positioned over a bottom side of an exterior wall of said reservoir;
   said reservoir coupled to said garment wherein said reservoir is configured to collect the urine from the infant, each of a first lateral edge and a second lateral edge of said bottom side of said exterior wall of said reservoir being penetrable by a syringe, each of said first and second lateral edges of said bottom side of said exterior wall of said reservoir being comprised of a resiliently penetrable material, said first flap being positionable in a closed position such that the urine is retained in said reservoir.

2. The assembly according to claim 1, further comprising said garment being elongated.

3. The assembly according to claim 1, further comprising said reservoir having said exterior wall extending between said top end and a bottom end of said reservoir, said top end of said reservoir being open.

4. The assembly according to claim 1, further comprising said top end of said reservoir being coupled to said bottom surface of said uppermost wall of said garment.

5. The assembly according to claim 1, further comprising said first flap being positionable in an open position to access an interior of said reservoir.

6. The assembly according to claim 1, further comprising said second flap being positionable between an open position and a closed position.

7. A urine collection assembly comprising:
   a garment having a first end and a second end, said garment being elongated, said garment having an uppermost wall and a bottommost wall each extending between said first and second ends of said garment, said garment being configured to be worn about the infant's genital area;
   a reservoir having an exterior wall extending between a top end and a bottom end of said reservoir, said top end of said reservoir being open, said top end of said reservoir being coupled to a bottom surface of said uppermost wall of said garment wherein said reservoir is configured to collect the urine from the infant;
   each of a first lateral edge and a second lateral edge of a bottom side of said exterior wall of said reservoir being penetrable by a syringe;
   each of said first and second lateral edges of said bottom side of said exterior wall of said reservoir being comprised of a resiliently penetrable material;
   said uppermost wall of said garment having a first flap positioned over said top end of said reservoir, said first flap being positionable in a closed position such that the urine is retained in said reservoir, said first flap being positionable in an open position to access an interior of said reservoir; and
   said lowermost wall of said garment having a second flap positioned over said bottom side of said exterior wall of said reservoir, said second flap being positionable between an open position and a closed position.

* * * * *